United States Patent [19]
Nederlof

[11] Patent Number: 5,846,419
[45] Date of Patent: Dec. 8, 1998

[54] HEMO(DIA)FILTRATION APPARATUS

[75] Inventor: Bernd Nederlof, St. Wendel, Germany

[73] Assignee: Fresenius AG, Bad Homburg, Germany

[21] Appl. No.: 891,267

[22] Filed: Jul. 10, 1997

Related U.S. Application Data

[63] Continuation of Ser. No. 501,383, Jul. 12, 1995, abandoned.

[30] Foreign Application Priority Data

Jul. 13, 1994 [DE] Germany ............................ 44 24 692.7

[51] Int. Cl.$^6$ .............................. B01D 61/26; B01D 61/28
[52] U.S. Cl. ....................... 210/323.1; 210/252; 210/258; 210/321.65; 210/409; 210/418; 210/433.1; 210/435; 210/646
[58] Field of Search .................................. 210/198.1, 201, 210/202, 203, 252, 254, 258, 295, 307, 321.6, 321.65, 321.72, 323.1, 409, 343, 417, 418, 420, 433.1, 435, 646, 645, 650, 929

[56] References Cited

U.S. PATENT DOCUMENTS 4,702,829 10/1987 Polaschegg et al. ............... 210/321.72
4,834,888 5/1989 Polaschegg ......................... 210/321.72
5,476,592 12/1995 Simard ................................ 210/321.69

FOREIGN PATENT DOCUMENTS 0042 939 1/1982 European Pat. Off. .
34 48 262 6/1990 Germany .

*Primary Examiner*—John Kim
*Attorney, Agent, or Firm*—Townsend & Townsend & Crew LLP; Kenneth R. Allen

[57] ABSTRACT

A hemo(dia)filtration apparatus (10) is described comprising a dialyzer (12) and two sterile filters (38) and (60). The first chambers (42) and (64) of both sterile filters (38) and (60) may be switched at least intermittently during flow through, thereby flushing out membranes (40) and (62) of both sterile filters (38) and (60) and effectively preventing an accumulation of germs and pyrogens. This prevents an increase in the transmembrane pressure (TMP), which reduces the likelihood of a rupture, thereby ensuring sterility of the dialyzer fluid and improving the operating safety of the hemodiafiltration apparatus (10).

19 Claims, 2 Drawing Sheets

HEMO(DIA)FILTRATION APPARATUS

This is a continuation of application Ser. No. 08/501,383, filed Jul. 12, 1995 now abandoned, the disclosure of which is incorporated by reference.

BACKGROUND OF THE INVENTION

The invention relates to a hemo(dia)filtration apparatus comprising a dialyzer divided by a membrane into two chambers, in which the first chamber is connected into a dialyzer fluid path and the second chamber is connected into a blood path, the dialyzer fluid path being comprised of a supply line extending from a means for preparing the dialyzer to a blood filter and into which a first balance chamber is connected, and a discharge line extending from the blood filter to a drain and into which a second balance chamber is connected; a pump for conveying dialyzer fluid within a closed dialyzer fluid system; a bypass line connecting the supply line with the discharge line of the dialyzer fluid path, in which a bypass valve is arranged; an ultrafiltration device; a first sterile filter incorporated in the supply line between the first balance chamber and the blood filter which is divided by a germ-repelling membrane into a first and a second chamber; and a second sterile filter divided by a germ-repelling membrane into a first and a second chamber.

Similar to hemodialysis, blood is conducted during hemofiltration past the membrane of a hemofilter, in which part of the serum is withdrawn via the membrane and replaced by a sterile substitution fluid added to the extracorporeal blood path either upstream of the dialyzer (predilution) or downstream (post dilution) of the dialyzer. In addition, in the hemodiafiltration, the usual hemodialysis is carried out, i.e. dialyzer fluid is conducted past the membrane of the hemodialyzer so that across the membrane an exchange of urophanic substances can take place.

Dialyzer fluid may be produced on-line from fresh water, and an electrolyte concentrate and the substitution fluid may be produced on-line from the dialyzer fluid. Though the electrolyte concentrate is as a rule inherently sterile and fresh water is generally germ-free, there is no certainty that the dialyzer fluid produced on-line is absolutely sterile and free of pyrogens, which is why the dialyzer fluid is rendered sterile and pyrogen-free for producing the substitute fluid. To achieve this, dialyzer fluid is removed via a line upstream of the blood filter, into which line at least one sterile filter is connected.

An apparatus of the this type is known, for example, from DE 34 44 671A or EP 0 042 939.

Due to a so-called "dead-end" arrangement of the sterile filter in the substituate line, the above-mentioned apparatuses have the drawback that in the course of time particles and other substances, e.g. imported germs and pyrogens, accumulate in front of the sterile filter membrane. This is especially dangerous if, as a result of a rupture, these substances can suddenly be carried into the sterile region, thereby contaminating the substitution fluid.

Thus, the object of the present invention is to further develop a hemodiafiltration apparatus of the aforementioned kind in such a way that clogging of the sterile filter with germs or pyrogens is largely eliminated, the safety of the hemodiafiltration apparatus is significantly improved and the sterility of the dialyzer fluid and the substituate is ensured through prevention of ruptures.

SUMMARY OF THE INVENTION

The object of the present invention is achieved in that the first chamber of the second sterile filter can be switched at least intermittently during flow through.

With the arrangement of the second sterile filter according to the present invention dialyzer fluid is allowed to flow through the first chamber and thus to at least intermittently flush the membrane of the second sterile filter, thereby preventing accumulation of germs and pyrogens in front of the membrane pores.

In an advantageous development of the hemodiafiltration apparatus according to the present invention, the first sterile filter is connected into the supply line and the first chamber of the first sterile filter can also be switched at least intermittently during flow through.

In addition, according to an advantageous development of the present invention, the first chamber of the first sterile filter is connected to the bypass line leading to the discharge line.

This arrangement of the first sterile filter results in a sterilizing filtration action of the dialyzer fluid, such that a completely sterile dialyzer fluid is conveyed to the following second sterile filter. Opening the bypass valve, which may be open during treatment and as the entire apparatus is being flushed, permits the dialyzer fluid to drain out of the first chamber of the sterile filter carrying with it any pyrogens and particles on the membrane into the discharge line and from there into the drain. It is thus feasible to flush the membrane at predetermined intervals, thereby reliably preventing accumulation of germs and pyrogens. Clogging of the membrane which results in an elevated transmembrane pressure is a principle cause of ruptures, hence, the likelihood of a rupture is lessened thereby, and this ensures the sterility of the dialyzer fluid and improves the safety of the hemodiafiltration apparatus.

According to a preferred embodiment of the present invention, the outlet of the first chamber of the second sterile filter is connected to the inlet of the first chamber of the dialyzer. With the inventive arrangement of a second sterile filter the dialyzer fluid which is shunted off as a substituate solution is subjected to a second, sterilizing filtration action to thereby effectively prevent contamination of the substituate solution should any leak occur in the membrane of the first sterile filter. In addition, by means of this inventive arrangement the membrane of the second sterile filter is continually flushed by dialyzer fluid flowing through the first chamber, thereby effectively preventing an accumulation of transported germs and pyrogens. The danger of a rupture is also considerably reduced, thus ensuring the sterility of the substituate solution and significantly improving the safety of the hemodiafiltration apparatus.

According to a yet another advantageous embodiment of the present invention, the outlet of the first chamber of the second sterile filter is connected to the discharge line of the dialyzer fluid path. A shut-off device and a venting device are advantageously connected into the connecting line between the first chamber of the second sterile filter and the discharge line of the dialyzer fluid path, so that opening said shut-off device allows the membrane of the second sterile filter to be flushed. Thus, in this embodiment the accumulation of germs and pyrogens is also effectively prevented and the danger of rupture is considerably reduced, such that the present arrangement ensures sterility of the substituate solution and it offers a high level of operating safety.

Thus, on the whole, a hemodiafiltration apparatus is provided which uses a two-fold safety means to effectively prevent contamination of blood in the dialyzer as well as contamination of the substituate solution due to transported germs or pyrogens. Moreover, the accumulation of pyrogens is effectively prevented, thereby providing a hemodiafiltration apparatus with a high level of operating safety.

According to the present invention a "balancing apparatus" is defined as a system which enables conveyed and discharged quantities of fluid to be precisely measured volumetrically (balanced) in relation to one other. Balancing apparatuses of this type are known, for example, from German patent publication DE 28 38 414, to which reference is made here, and which contain conventional balance chambers as balancing units having a defined interior volume. Also, a balancing unit in accordance with the present invention may refer to other devices which have a balancing function, e.g. balancing pumps and the like.

BRIEF DESCRIPTION OF THE DRAWINGS

Further details, features and advantages of the present invention are explained with the aid of the following description of two embodiments with reference to the drawings, in which

In FIG. 1 the numeral 10 denotes a hemodiafiltration apparatus which comprises a conventional dialyzer 12 divided by a membrane 18 into a first chamber 14 through which dialyzer fluid flows and a second chamber 16 through which blood flows.

DESCRIPTION OF THE PREFERRED EMBODIMENT

Figure 1:
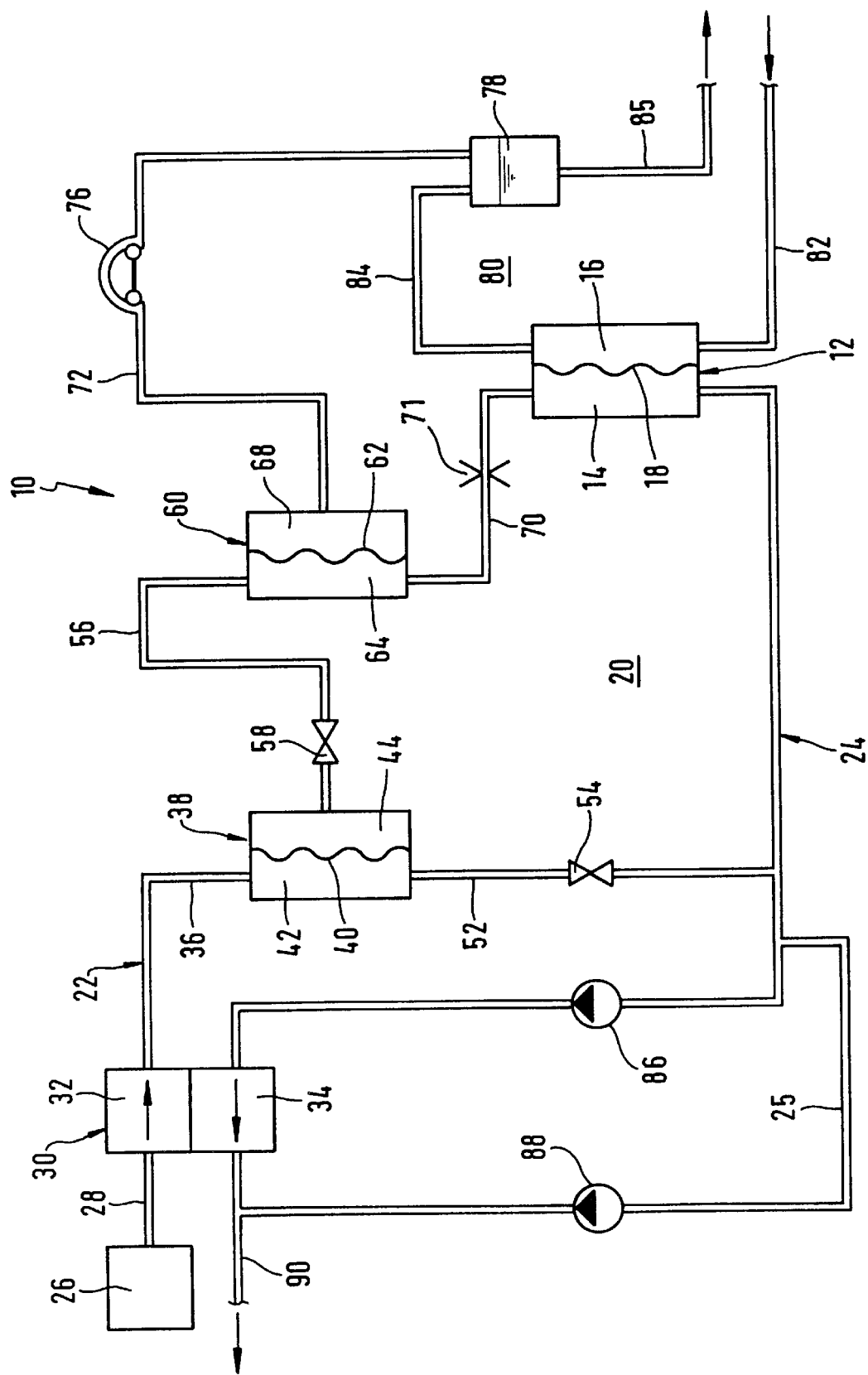
FIG. 1 is a schematic representation of a first embodiment of the hemodiafiltration apparatus according to the present invention.

The first chamber 14 is connected into a dialyzer fluid path 20 consisting of a supply line 22 and a discharge line 24, and the second chamber 16 is connected into a blood path 80.

Supply line 22 consists of a first supply line section 28, a second supply line section 36, a third supply line section 56 and a fourth supply line section 70, and connects a dialyzer fluid source 26 to the first chamber 14 of the dialyzer 12.

The first supply line section 28 connects the dialyzer fluid source 26 to the first chamber (balancing unit) 32 of a balancing apparatus 30. The first chamber 32 of the balancing apparatus 30 is connected via the second supply line section 36 to the first chamber 42 of a first sterile filter 38. The first sterile filter 38 is divided by a membrane 40 into a first chamber 42 and a second chamber 44. The outlet of the first chamber 42 of the first sterile filter 38 is connected to a bypass line 52, into which a bypass valve 54 is connected and which is connected to the discharge line 24.

The third supply line section 56 branches off the second chamber 44 of the first sterile filter 38 and is connected to the first chamber 64 of a second sterile filter 60. A valve 58 is connected into the third supply line section 56. The second sterile filter 60 is divided by a membrane 62 into a first chamber 64 and a second chamber 68. The outlet of the first chamber 64 of the second sterile filter 60 is connected to the fourth supply line section 70 which leads to the first chamber 14 of the dialyzer 12.

Discharge line 24 leads from the outlet of the first chamber 14 of dialyzer 12 to the second balance chamber (balancing unit) 34 of the balancing apparatus 30. A dialyzer fluid pump 86 is connected into discharge line 24, further an ultrafiltration line 25 branches off discharge line 24 into which an ultrafiltration pump 88 is connected. Ultrafiltration line 25 leads to a drain 90, to which the outlet of the second balance chamber 34 of balancing apparatus 30 is attached.

The second chamber 16 of the dialyzer 12 is connected into the blood path in such a way that blood supply line 82 originating from the patient is attached to the inlet of the first chamber 16 and a first section 84 of a blood discharge line is attached to the outlet of the first chamber 16. The first section 84 of the blood discharge line leads to a drip chamber 78 at which point the blood is routed via a second section 85 of the blood discharge line back to the patient.

Branching off the second chamber 68 of the second sterile filter 60 is a substituate line 72 into which a substituate pump 76 is connected, and which also leads to drip chamber 78.

Fresh dialyzer fluid is conveyed from the dialyzer fluid source 26 through the first supply line section 28 to the first chamber 32 of the balancing apparatus 30. Said first balance chamber 32 is connected to the supply line 22 of the dialyzer fluid path 20, so that the fresh dialyzer fluid is conducted from the first balance chamber 32 through the second supply line section 36, through sterile filter 38, through the third supply line section 56, through the first chamber 64 of the second sterile filter 60 and through the fourth supply line section 70 to the first chamber 14 of the dialyzer 12. The dialyzer fluid, as it passes through the membrane 40 of the first sterile filter 38, is subjected to a sterilizing filtration action so that fully sterilized dialyzer fluid is conducted into the first chamber 14 of the dialyzer 12. The outlet of the first chamber 14 of dialyzer 12 is connected to discharge line 24 which leads to the second balance chamber 34 of the balancing apparatus 30. A dialyzer fluid pump 86 is incorporated in said discharge line 24 which conveys the dialyzer fluid into the dialyzer fluid path 20 from the first balance chamber 32 to the second balance chamber 34 of balancing apparatus 30. Balancing apparatus 30 is designed so that a quantity of used dialyzer fluid flowing through the second balance chamber 34 into drain 90 is replaced by an equal amount of fresh dialyzer fluid conveyed through the first balance chamber 32 into supply line 22. A shut-off device 71 in the form of a regulator clamp is connected into the fourth supply line section 70, with which said supply line section 70 may be shut off when necessary. When this occurs the apparatus 10 then functions exclusively as a hemofiltration apparatus.

Thus, in accordance with yet a further inventive concept, clamp 71 may be closed whenever a hemofiltration arrangement alone is desired, and may be opened solely for the purpose of flushing membrane 62. In such an embodiment it is also feasible to route supply line 70 either directly to the outlet or to connect it directly to the discharge line 24, so that the inlet of the first chamber 14 of blood filter 12 is closed. During hemofiltration, then, a hemofilter is preferably used in place of a dialyzer 11.

Said clamp 71 may be sequentially opened and closed in accordance with a program. According to yet another embodiment of the present invention the clamp 71 may be activated in such a way that it constricts or expands incrementally the diameter of line 70. As a result varying fluid amounts are allowed to pass through causing a corresponding decrease or increase in the fluid flow through membrane 62. Optionally, this may be effected in synchrony with pump 76.

Germs and pyrogens transported in the fresh dialyzer fluid into supply line 22 are filtered out by membrane 40 of sterile filter 38 and adhere to same. Opening bypass valve 54 in bypass line 52 which forms a link between the first chamber 42 and discharge line 24, causes the first chamber 42 to be flushed with dialyzer fluid. This causes particles, germs and pyrogens that have accumulated on membrane 40 to be carried away by the dialyzer fluid flowing past said membrane and to be flushed through the second balance chamber 34 and into drain 90 by way of bypass line 52 and discharge line 24. This permits effective flushing of membrane 40 of sterile filter 38, thereby considerably reducing the danger of rupture and ensuring sterility of the dialyzer fluid, which results in an arrangement with a high degree of operating safety.

By activating substitute pump 76, dialyzer fluid which flows through the first chamber 64 is drawn through membrane 62 into the second chamber 68 and from there passes into substituate line 72. Said substituate line 72 leads to a drip chamber 78 which is connected into blood path 80. Also emptying into drip chamber 78 is a first blood discharge line section 84 one end of which is attached to the outlet of the second chamber 16 of dialyzer 12 and the other end of which empties into drip chamber 78. A second blood discharge line 85 leads from drip chamber 78 to the patient. It is understood that in addition to predilution as it is represented here, postdilution is also possible.

Moreover, ultrafiltrate pump 88 may be activated to remove fluid from the closed, hydraulic dialyzer fluid path, which is then drawn through membrane 18 of dialyzer 12 and out of the blood flowing through the second chamber 16.

Such an arrangement firstly yields two-fold protection against blood contamination. Secondly, flushing both membrane 40 of the first sterile filter 38 and membrane 62 of the second sterile filter 60 prevents an accumulation of germs and pyrogens on these membranes, thereby reducing considerably the danger of a rupture proximate any of said membranes. This ensures a continuous, absolutely sterile flow of substituate solution to the patient.

Figure 2:
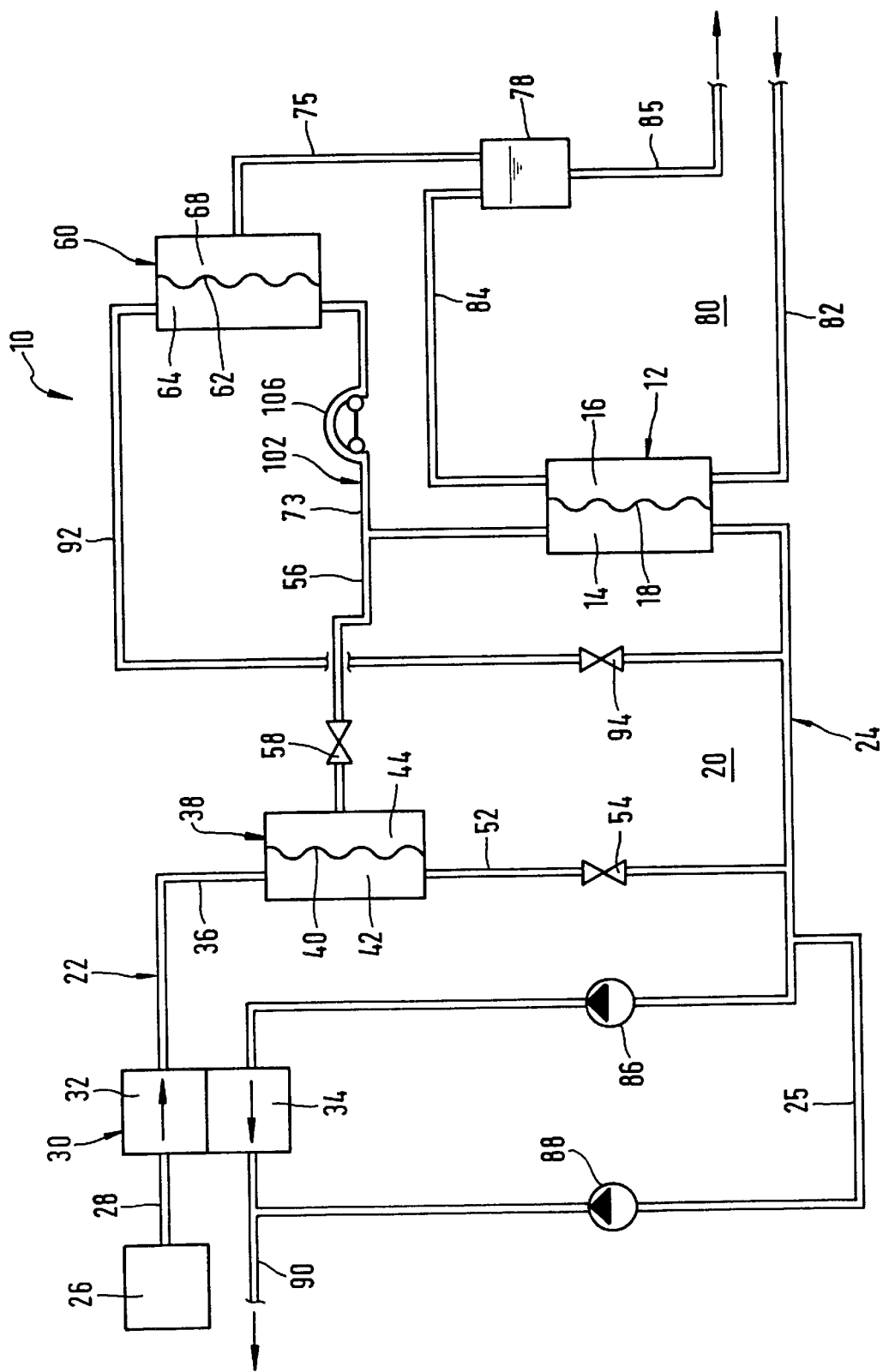
FIG. 2 is a schematic representation of a second embodiment of the hemodiafiltration apparatus according to the present invention.

FIG. 2 shows a second embodiment of hemodiafiltration apparatus 10 according to the present invention, which is in large part identical to the embodiment of FIG. 1, such that identical parts are labelled with identical reference numerals and no further detailed description is necessary.

In this second embodiment dialyzer fluid path 20 between blood filters 12 and 60 is modified as compared with the embodiment of FIG. 1, to the extent that the third supply line section 56 of supply line 22 leads from the second chamber 44 of the first sterile filter 38 to the first chamber 14 of dialyzer 12. Substituate line 102 branches off the third supply line section 56 and leads via first supply line section 73, into which substituate pump 106 is connected, to first chamber 64 of the second sterile filter 60. The second supply line section 75 of substituate line 102 then leads from the second chamber 68 of sterile filter 60 to drip chamber 78. Branching off the outlet of the first chamber 64 of the second sterile filter 60 is a connecting line 92 which is connected to discharge line 24 of the dialyzer fluid path 20. Connected into said connecting line 92 is a shut-off valve 94.

The hemodiafiltration apparatus according to FIG. 2 functions in essentially the same manner as the embodiment according to FIG. 1 described in detail above, such that no detailed description of the operation of the latter embodiment is necessary here. The basic difference with respect to the embodiment described above is that the outlet of the second chamber 44 of the first sterile filter 38 is directly connected to the first chamber 14 of the dialyzer, so that the dialyzer fluid does not flow permanently through the first chamber 64 of the second sterile filter 60. The substituate line 102 in this embodiment is designed in such a way that a first substituate line section 73 branches off the third supply line section 56 and is routed to the second sterile filter 60. A substituate pump 106 is incorporated in said first substituate line section 73, which removes dialyzer fluid from the dialyzer fluid path 20. Said fluid is then sterilized by being filtered through membrane 62 of the second sterile filter 60 and conveyed by means of a second substituate line section 75 to the drip chamber 78 which, as described above, is incorporated in blood path 80. In order to flush out membrane 62 of the second sterile filter 60, the outlet of the first chamber 64 is connected to the discharge line 24 via connecting line 92, thus providing, in a sense, a second bypass line. A shut-off device 94 is incorporated in connecting line 92, such that by opening said shut-off device 94 dialyzer fluid may be conducted through the first chamber 64 in order to thereby flush out membrane 62.

What is claimed is:
1. A hemo(dia)filtration apparatus comprising:
a dialyzer divided by a dialyzer membrane into a first dialyzer chamber and a second dialyzer chamber, in which the first dialyzer chamber is part of a dialyzer fluid path and the second dialyzer chamber is part of a blood path, the dialyzer fluid path being comprised of a supply line (22) extending from a means for preparing dialysis fluid to the dialyzer and a discharge line extending from the dialyzer to a drain;
a balancing unit having a first balancing unit chamber (32) and a second balancing unit chamber (34), the first balancing unit chamber (32) being connected into the supply line (22) and the second balancing unit chamber (34) being connected into the discharge line (24);
a pump for conveying dialyzer fluid within a closed dialyzer fluid system, a bypass line connecting the supply line to the discharge line of the dialyzer fluid path, into which a bypass valve is connected;
a first sterile filter being divided by a first germ-repelling membrane into a first sterile filter chamber and a second sterile filter chamber, the first sterile filter chamber being configured to receive dialyzer fluid from the first balancing unit chamber via a section of the supply line;
at least one second sterile filter, the second sterile filter being divided by a second germ-repelling membrane into a third sterile filter chamber (64) and a fourth sterile filter chamber (68);
a substituate line extending from a fourth outlet of the fourth sterile filter chamber to the blood path;
wherein an inlet of the third sterile filter chamber (64) of the at least second sterile filter (60) is connected to a second outlet of the second sterile filter chamber of the first sterile filter and a third outlet of the third sterile filter chamber of the at least second sterile filter is connected to an inlet of the first dialyzer chamber.

2. Hemo(dia)filtration apparatus according to claim 1, wherein the first sterile filter chamber (42) of the first sterile filter (38) comprises a flushing means (52, 54) for flushing the first germ-repelling membrane.

3. Hemo(dia)filtration apparatus according to claim 1 wherein the first outlet of the first sterile filter chamber (42) of the first sterile filter (38) is capable of being selectively coupled to the discharge line (24) through the bypass line (52) by the operation of the bypass valve (54).

4. Hemo(dia)filtration apparatus according to claim 1, characterized in that the third outlet of the third sterile filter chamber (64) of the second sterile filter (60) is connected via a further supply line section (70) of the supply line (22) to the inlet of the first dialyzer chamber (14).

5. Hemo(dia)filtration apparatus according to claim 4, further comprising a shut-off device (71) connected into the further supply line section (70), the shut-off device being capable of constricting flow through the further supply line section (70) in a predetermined manner.

6. A hemo(dia)filtration apparatus comprising:
a dialyzer divided by a dialyzer membrane into into a first dialyzer chamber and a second dialyzer chamber, in which the first dialyzer chamber is connected into a dialyzer fluid path and the second dialyzer chamber is connected into a blood path, the dialyzer fluid path being comprised of a supply line (22) extending from a means for preparing dialysis fluid to an inlet of the first dialyzer chamber of the dialyzer and a discharge line extending from the dialyzer to a drain;
a balancing unit having a first balancing unit chamber (32) and a second balancing unit chamber (34), the first balancing unit chamber (32) being connected into the supply line (22) and the second balancing unit chamber (34) being connected into the discharge line (24);

a pump for conveying dialyzer fluid within a closed dialyzer fluid system, a bypass line capable of selectively coupling the supply line to the discharge line by operation of a bypass valve disposed in the bypass line;

a first sterile filter being divided by a first germ-repelling membrane into a first sterile filter chamber and a second sterile filter chamber, the first sterile filter chamber being configured to receive dialyzer fluid from the first balancing unit chamber via a section of the supply;

at least one second sterile filter (60) divided by a germ-repelling membrane (62) into a third sterile filter chamber (64) and a fourth sterile filter chamber (68);

a substitute line extending from an outlet of the fourth sterile filter chamber of the at least second sterile filter to the blood path;

wherein an inlet of the third sterile filter chamber (64) of the at least second sterile filter (60) is connected to a second outlet of the second sterile filter chamber with a first connecting line (73) branching off a section of the supply line (56) connecting the second outlet to the dialyzer, characterized in that a third outlet of the third sterile filter chamber (64) of the second sterile filter (60) is connected via a second connecting line (92) to the discharge line (24) of the dialyzer fluid path (20).

7. Hemo(dia)filtration apparatus according to claim 6 further comprising a shut-off device (94) disposed in the second connecting line (92) between the second sterile filter (60) and the discharge line (24).

8. Hemo(dia)filtration apparatus according to claim 1 or 6, further comprising a shut-off device (58) connected into a supply line portion (56) downstream from the second outlet of the first sterile filter (38).

9. A hemo(dia)filtration apparatus according to claim 6 wherein a first outlet of the first sterile filter chamber of the first sterile filter is capable of being selectively coupled to the discharge line through the bypass line by the operation of a bypass valve.

10. A hemo(dia)filtration apparatus comprising:

a dialyzer divided by a dialyzer membrane into a first dialyzer chamber and a second dialyzer chamber, in which the first dialyzer chamber is connected into a dialyzer fluid path and the second dialyzer chamber is connected into a blood path, the dialyzer fluid path being comprised of a supply line extending from a means for preparing the dialyzer fluid to the dialyzer, a first balancing unit chamber connected to said supply line, a discharge line extending from the dialyzer to a second balancing unit chamber, the second balancing unit chamber being connected to a drain;

a pump for conveying dialyzer fluid within a closed dialyzer fluid system, a bypass line capable of selectively coupling the supply line to the discharge line by operation of a bypass valve disposed in the bypass line;

an ultrafiltration device selectively connecting the discharge line to the drain;

a first sterile filter which is divided by a first germ-repelling membrane into a first sterile filter chamber and a second sterile filter chamber, said first sterile filter chamber (42) of the first sterile filter (38) having a first inlet connected to the supply line leading from the first balancing unit chamber, and having a first outlet connected to the bypass line (52), and said second sterile filter chamber of the first sterile filter having a second outlet connected to the dialyzer with the supply line;

a connecting line coupling the second sterile filter chamber to the first dialyzer chamber;

at least a second sterile filter, said second sterile filter being divided by a second germ-repelling membrane into a third sterile filter chamber and a fourth sterile filter chamber, said third sterile filter chamber of the second sterile filter having a third inlet connected to the supply line leading from the second outlet and having a third outlet connected to the supply line leading to the dialyzer and said fourth sterile filter chamber of the second sterile filter having a fourth outlet connected to a substitute line leading to the blood path;

wherein the first sterile filter chamber (42) of said first sterile filter (38) is switched at least intermittently during flow through by opening the bypass valve (54) in the bypass line to flush the first sterile filter chamber with dialysis fluid; and wherein the third sterile filter chamber (64) of the second filter (60) is flushed at least intermittently during flow through by operation of a flushing means (70, 71), the flushing means being disposed between a third outlet of the third sterile filter chamber and the discharge line.

11. A hemo(dia)filtration apparatus comprising:

a dialyzer divided by a dialyzer membrane into a first dialyzer chamber and a second dialyzer chamber, in which the first dialyzer chamber is connected into a dialyzer fluid path and the second dialyzer chamber is connected into a blood path, the dialyzer fluid path being comprised of a supply line extending from a means for preparing the dialyzer fluid to the dialyzer, a first balancing unit chamber connected to said supply line, a discharge line extending from the dialyzer to a drain and a second balancing unit chamber connected to said discharge line;

a pump for conveying dialyzer fluid within a closed dialyzer fluid system, a bypass line capable of selectively connecting the supply line to the discharge line by operation of a bypass valve disposed in the bypass line;

an ultrafiltration device capable of selectively coupling the discharge line to the drain;

a first sterile filter which is divided by a first germ-repelling membrane into a first sterile filter chamber and a second sterile filter chamber, said first sterile filter chamber of the first sterile filter having a first inlet connected to the supply line leading from the first balancing unit chamber and a first outlet connected to the bypass line leading to the discharge line and said second sterile filter chamber of the first sterile filter having a second outlet connected to the supply line leading to the dialyzer;

a connecting line coupling the second sterile filter chamber to the first dialyzer chamber;

at least a second sterile filter, said second sterile filter being divided by a second germ-repelling membrane into a third sterile filter chamber and a fourth sterile filter chamber, said third sterile filter chamber (64) of the second sterile filter (60) having a third inlet connected to the supply line leading from the second outlet and a third outlet connected to the supply line leading to the first dialyzer chamber (14) and said fourth sterile filter chamber of the second sterile filter having a fourth outlet connected to a substitute line leading to the blood path;

wherein the third sterile filter chamber (64) of the second sterile filter (60) is switched at least intermittently during flow through by operation of a flushing means (70, 71), the flushing means being disposed between a third outlet of the third sterile filter chamber and the discharge line.

12. Hemo(dia)filtration apparatus according to claim 11, further comprising a shut-off device (71) connected into the supply line downstream from the second outlet capable of constricting a flow of dialyzer fluid into the first dialyzer chamber in a predetermined manner.

13. A hemo(dia)filtration apparatus comprising:

a dialyzer divided by a dialyzer membrane into a first dialyzer chamber and a second dialyzer chamber, in which the first dialyzer chamber is connected into a dialyzer fluid path and the second dialyzer chamber is connected into a blood path, the dialyzer fluid path being comprised of a supply line extending from a means for preparing the dialyzer fluid to the dialyzer, a first balancing unit chamber connected to said supply line, a discharge line extending from the dialyzer to a drain and a second balancing unit chamber connected to said discharge line;

a pump for conveying dialyzer fluid within a closed dialyzer fluid system, a bypass line capable of selectively connecting the supply line to the discharge line by operation of a bypass valve disposed in the bypass line;

an ultrafiltration device capable of selectively connecting the discharge line to the drain;

a first sterile filter divided by a first germ-repelling membrane into a first sterile filter chamber and a second sterile filter chamber, said first sterile filter chamber of the first sterile filter having a first inlet connected to the supply line leading from the first balancing unit chamber and a first outlet connected to the bypass line leading to the discharge line and said second sterile filter chamber of the first sterile filter having a second outlet connected to the supply line leading to the dialyzer;

a first connecting line (72) branching off the supply line to couple the second sterile filter chamber to a third sterile filter chamber of a second sterile filter, said second sterile filter being divided by a second germ-repelling membrane into the third sterile filter chamber and a fourth sterile filter chamber, said third sterile filter chamber (64) of the second sterile filter having a third inlet connected to the first connecting line and a third outlet connected via a second connecting line (92) to the discharge line (24) of the dialyzer fluid path (20) and said fourth sterile filter chamber of said second sterile filter having an outlet to the blood path;

wherein the third sterile filter chamber (64) of the second sterile filter (60) is switched at least intermittently during flow through by operation of a flushing means (92, 94), the flushing means being disposed between a third outlet of the third sterile filter chamber and the discharge line; and a shut-off device (94) being connected into the second connecting line (92) between the third outlet and the discharge line (24).

14. A hemo(dia)filtration apparatus comprising:

a dialyzer fluid source;

a first sterile filter separated by a first germ-repelling membrane into a first sterile filter chamber and a second sterile filter chamber;

a first portion of a supply line connecting the dialyzer fluid source to the first sterile filter chamber;

a second sterile filter separated by a second germ-repelling membrane into a third sterile filter chamber and a fourth sterile filter chamber;

a second portion of the supply line connecting the second sterile filter chamber to the third sterile filter chamber;

a dialyzer separated by a dialyzer membrane into a first dialyzer chamber and a second dialyzer chamber, the second dialyzer chamber being connected into a blood path;

a third portion of the supply line connecting the third sterile filter chamber to the first dialyzer chamber so that the second germ-repelling membrane is flushed by a flow of dialyzer fluid through the third sterile filter chamber;

a discharge line connecting the first dialyzer chamber to a drain; and a substitute line connecting the fourth sterile filter chamber to the blood path.

15. The apparatus of claim 14 further comprising a bypass line capable of selectively coupling the first sterile filter to the discharge line to flush the first germ-repelling membrane.

16. The apparatus of claim 14 further comprising a balancing unit having a first balancing unit chamber disposed between the dialyzer fluid source and the first sterile filter chamber, and a second balancing unit chamber disposed between the discharge line and the drain, and an ultrafiltration line capable of selectively connecting the discharge line to the drain to bypass the second balancing unit chamber.

17. A hemo(dia)filtration apparatus comprising:

a dialyzer fluid source;

a first sterile filter separated by a first germ-repelling membrane into a first sterile filter chamber and a second sterile filter chamber;

a first portion of a supply line connecting the dialyzer fluid source to the first sterile filter chamber;

a second sterile filter separated by a second germ-repelling membrane into a third sterile filter chamber and a fourth sterile filter chamber;

a dialyzer separated by a dialyzer membrane into a first dialyzer chamber and a second dialyzer chamber, the second dialyzer chamber being connected into a blood path;

a second portion of the supply line connecting the second sterile filter chamber to the first dialyzer chamber and a branch of the second portion of the supply line connecting the second sterile filter chamber to the third sterile filter chamber;

a substitute line connecting the fourth sterile filter chamber to the blood path;

a discharge line connecting the first dialyzer chamber to a drain; and a connecting line capable of selectively connecting the third sterile filter chamber to the discharge line to flush the second germ-repelling membrane.

18. The apparatus of claim 17 further comprising a bypass line capable of selectively coupling the first sterile filter to the discharge line to flush the first germ-repelling membrane.

19. The apparatus of claim 17 further comprising a balancing unit having a first balancing unit chamber disposed between the dialyzer fluid source and the first sterile filter chamber, and a second balancing unit chamber disposed between the discharge line and the drain, and an ultrafiltration line capable of selectively connecting the discharge line to the drain to bypass the second balancing unit chamber.

* * * * *